(12) United States Patent
Biedermann et al.

(10) Patent No.: US 11,937,852 B2
(45) Date of Patent: *Mar. 26, 2024

(54) POLYAXIAL BONE ANCHORING DEVICE WITH ENLARGED PIVOT ANGLE

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE); Tobias Hägle, Donaueschingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 226 days.

This patent is subject to a terminal disclaimer.

(21) Appl. No.: 17/404,239

(22) Filed: Aug. 17, 2021

(65) Prior Publication Data

US 2022/0031369 A1 Feb. 3, 2022

Related U.S. Application Data

(63) Continuation of application No. 16/259,373, filed on Jan. 28, 2019, now Pat. No. 11,116,546, which is a (Continued)

(30) Foreign Application Priority Data

Nov. 24, 2010 (EP) .................................. 10192373

(51) Int. Cl.
  *A61B 17/70* (2006.01)
(52) U.S. Cl.
  CPC ...... *A61B 17/7037* (2013.01); *A61B 17/7035* (2013.01)

(58) Field of Classification Search
  None
  See application file for complete search history.

(56) References Cited

U.S. PATENT DOCUMENTS

| 5,501,684 A | 3/1996 | Schlapfer |
| 6,736,820 B2 | 5/2004 | Biedermann et al. |

(Continued)

FOREIGN PATENT DOCUMENTS

| CN | 101652106 A | 2/2010 |
| CN | 101754725 A | 6/2010 |

(Continued)

OTHER PUBLICATIONS

European Search Report for corresponding European Application No. 10 192 373.8, European Search Report dated Apr. 21, 2011 and dated May 4, 2011 (5 pgs.).

(Continued)

*Primary Examiner* — Jan Christopher L Merene
(74) *Attorney, Agent, or Firm* — Lewis Roca Rothgerber Christie LLP

(57) ABSTRACT

A polyaxial bone anchoring device includes: an anchoring element having a shaft for anchoring in a bone and a head, the head having a spherically-shaped outer surface portion; a receiving part configured to be pivotably connected to the head, the receiving part having a top end and a bottom end, a longitudinal axis extending through the top end and the bottom end, a channel transverse to the longitudinal axis for receiving a rod, and an accommodation space for accommodating the head, the accommodation space having a lower opening at the bottom end, a sleeve-like insert piece configured to be positioned around a portion of the head and to pivot in the receiving part, the insert piece having a spherically-shaped outer surface portion, wherein a lower edge of the insert piece extends past the lower opening in a (Continued)

direction away from the receiving part when the insert piece is seated in the receiving part in a position in which a central axis of the insert piece is coaxial with the longitudinal axis, and wherein the insert piece has an opening with a diameter greater than or equal to a maximum diameter of the head when the head is not in contact with the insert piece; a pressure member configured to be arranged at least partially in the accommodation space, the pressure member having a lower surface portion configured to contact the head to exert pressure onto the head when the head and the pressure member are arranged in the receiving part; wherein when the head, the insert piece, and the pressure member are arranged in the receiving part, the insert piece is tiltable with respect to the longitudinal axis of the receiving part and with respect to a longitudinal axis of the anchoring element, and wherein the anchoring element and the insert piece can be locked at respective angles relative to the longitudinal axis of the receiving part by exerting pressure with the pressure member onto the head.

20 Claims, 14 Drawing Sheets

Related U.S. Application Data continuation of application No. 15/676,795, filed on Aug. 14, 2017, now Pat. No. 10,231,758, which is a continuation of application No. 13/304,228, filed on Nov. 23, 2011, now Pat. No. 9,763,698.

(60) Provisional application No. 61/417,167, filed on Nov. 24, 2010.

(56) References Cited

U.S. PATENT DOCUMENTS

| | | | |
|---|---|---|---|
| 7,476,239 B2 | 1/2009 | Jackson | |
| 7,776,067 B2 | 8/2010 | Jackson | |
| 7,794,482 B2 | 9/2010 | Mathieu | |
| 8,961,568 B2 | 2/2015 | McKinley et al. | |
| 9,247,965 B2 | 2/2016 | Biedermann et al. | |
| 2003/0167058 A1 | 9/2003 | Shluzas | |
| 2005/0049588 A1 | 3/2005 | Jackson | |
| 2005/0203516 A1 | 9/2005 | Biedermann et al. | |
| 2005/0216003 A1 | 9/2005 | Biedermann et al. | |
| 2006/0084979 A1 | 4/2006 | Jackson | |
| 2006/0173456 A1 | 8/2006 | Hawkes et al. | |
| 2006/0271047 A1 | 11/2006 | Jackson | |
| 2007/0049933 A1 | 3/2007 | Ahn et al. | |
| 2007/0118123 A1 | 5/2007 | Strausbaugh et al. | |
| 2007/0123862 A1 | 5/2007 | Warnick | |
| 2008/0009862 A1 | 1/2008 | Hoffman | |
| 2008/0015579 A1 | 1/2008 | Whipple | |
| 2008/0132957 A1 | 6/2008 | Matthis | |
| 2008/0154315 A1 | 6/2008 | Jackson | |
| 2008/0172094 A1 | 7/2008 | Mathieu | |
| 2008/0177260 A1 | 7/2008 | McKinley et al. | |
| 2008/0234761 A1 | 9/2008 | Jackson | |
| 2009/0093844 A1 | 4/2009 | Jackson | |
| 2009/0240290 A1 | 9/2009 | Choi | |
| 2010/0030280 A1 | 2/2010 | Jackson | |
| 2010/0191293 A1 | 7/2010 | Jackson | |
| 2010/0211114 A1 | 8/2010 | Jackson | |
| 2010/0298891 A1 | 11/2010 | Jackson | |
| 2012/0123486 A1 | 5/2012 | Werner | |
| 2012/0179212 A1 | 7/2012 | Jackson et al. | |
| 2013/0096620 A1 | 4/2013 | Biedermann et al. | |
| 2014/0121703 A1 | 5/2014 | Jackson et al. | |
| 2014/0128927 A1 | 5/2014 | Jackson | |

FOREIGN PATENT DOCUMENTS

| | | |
|---|---|---|
| JP | 2006-504505 A | 2/2006 |
| JP | 2010-520024 A | 6/2010 |
| KR | 10-0980459 B1 | 9/2010 |
| WO | WO 2004/041100 A1 | 5/2004 |
| WO | WO 2008/112114 A1 | 9/2008 |
| WO | WO 2008/124772 A1 | 10/2008 |
| WO | WO 2008/153723 A1 | 12/2008 |
| WO | WO 2009/015100 A2 | 1/2009 |

OTHER PUBLICATIONS http://dictionary.reference.com/browse/continuous, definition of "continuous" accessed Feb. 18, 2016.

http://www.thefreedictionary.com/ring, definition of "ring," accessed Aug. 25, 2015.

Japanese Office action for Application No. 2011-254090 dated May 26, 2015 (4 pages) and English translation (6 pages).

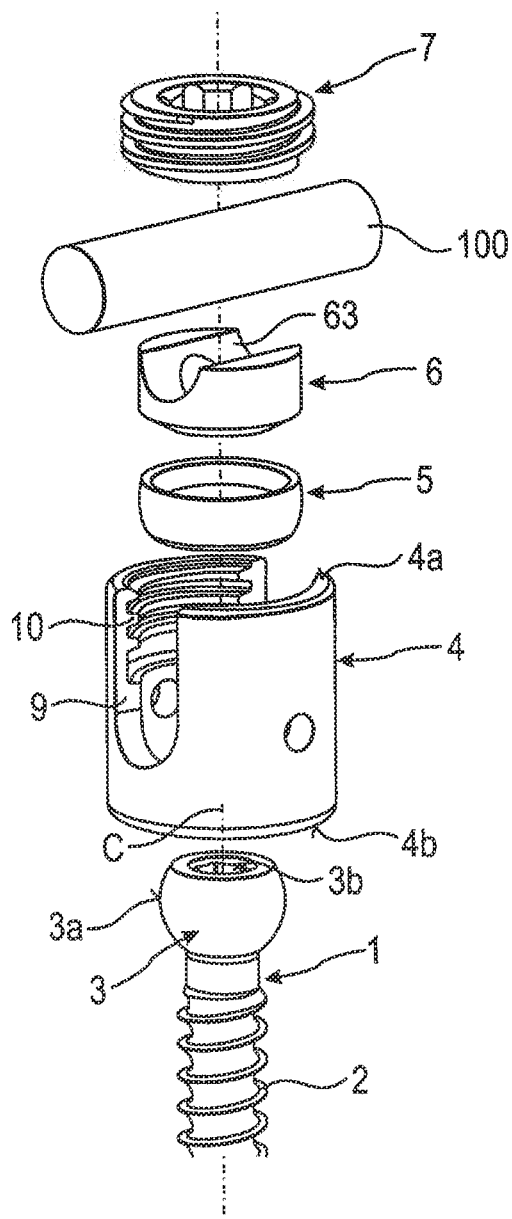
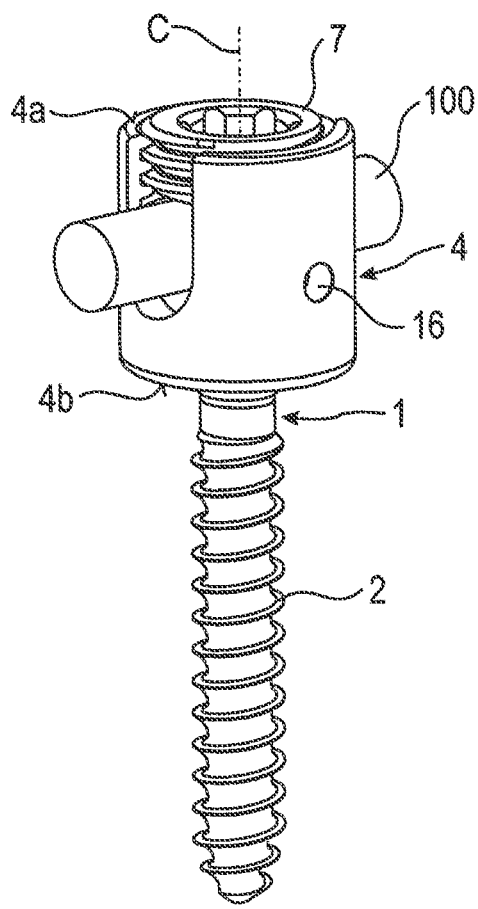

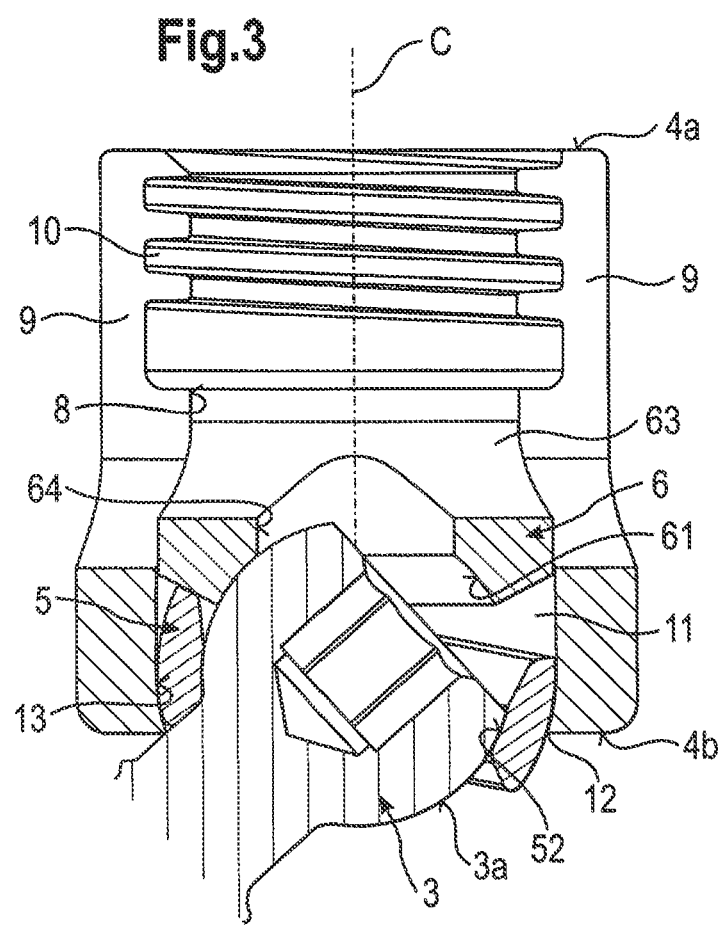

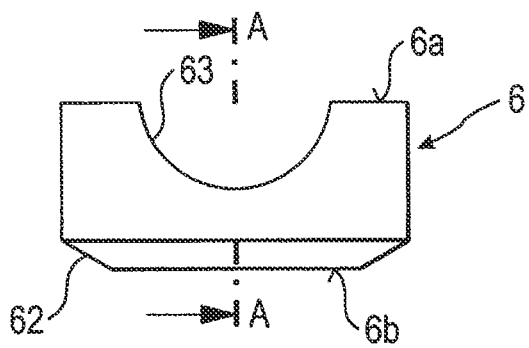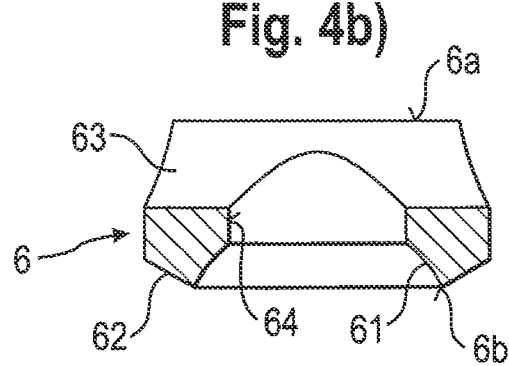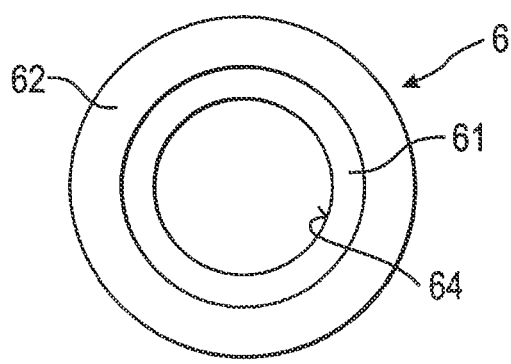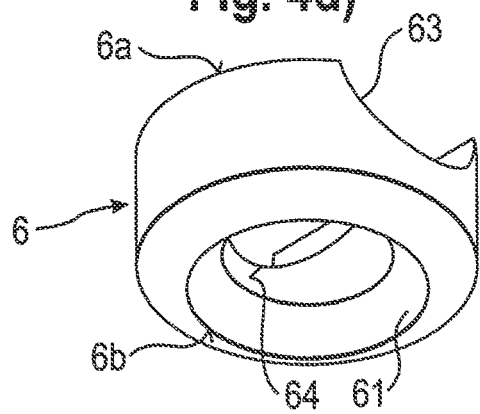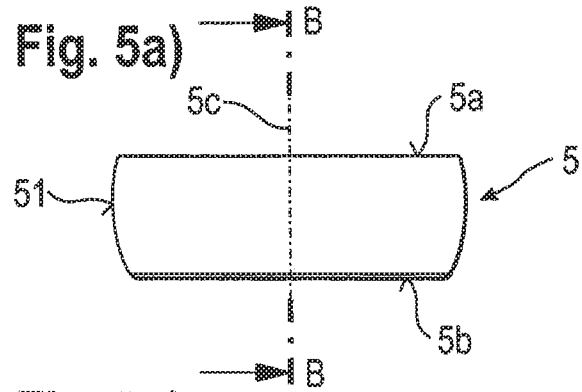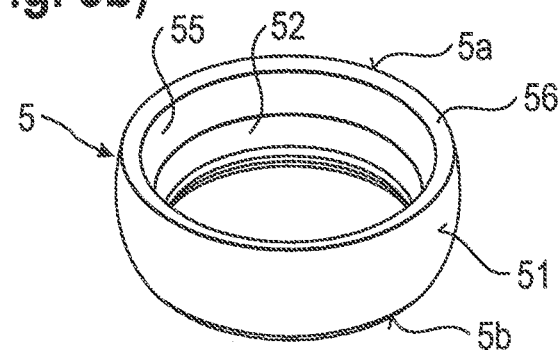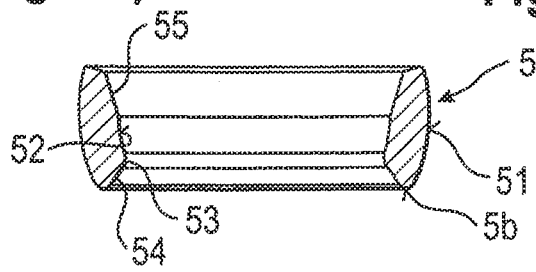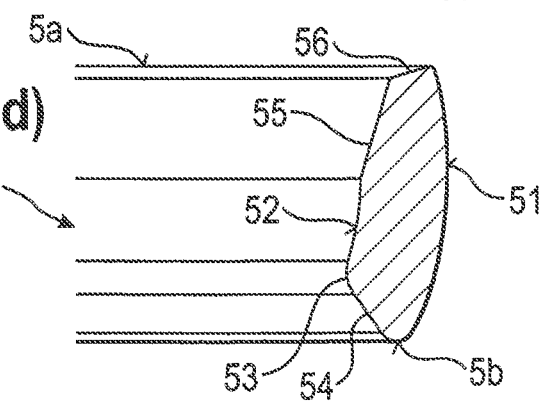

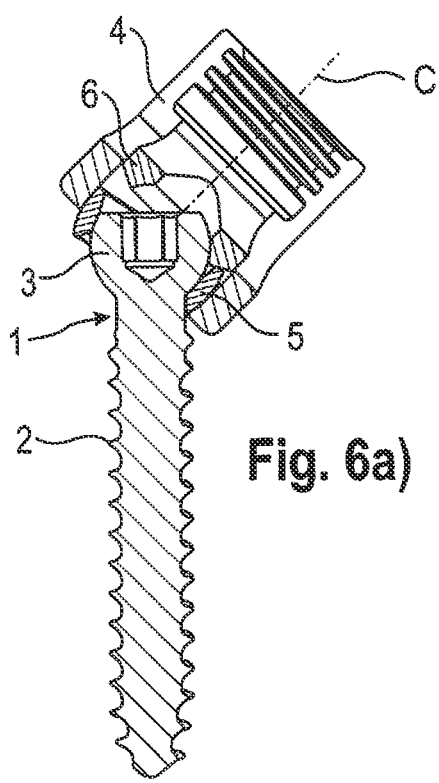
Fig. 6a)
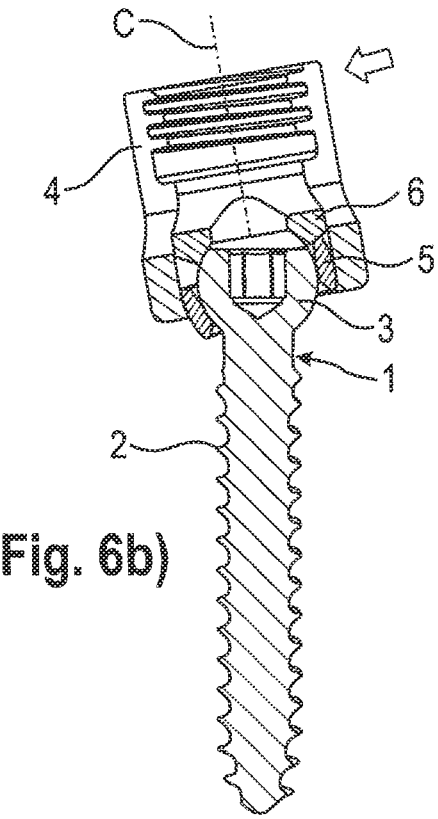
Fig. 6b)
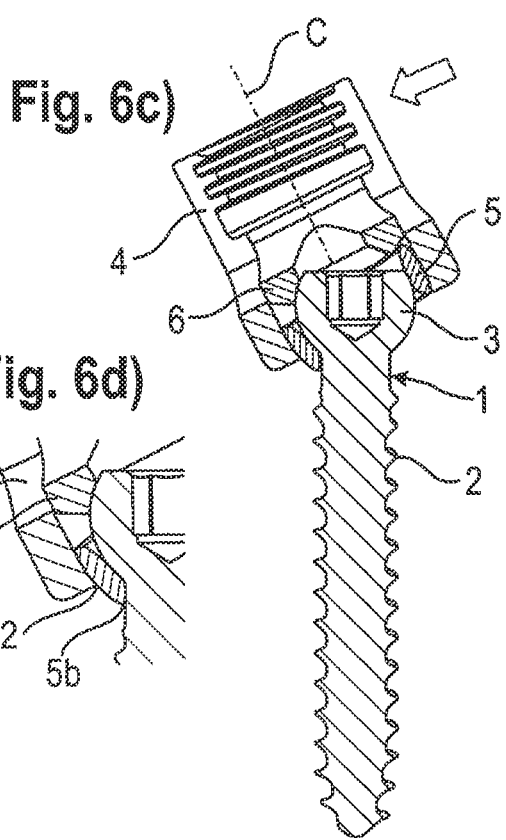
Fig. 6c)
Fig. 6d)
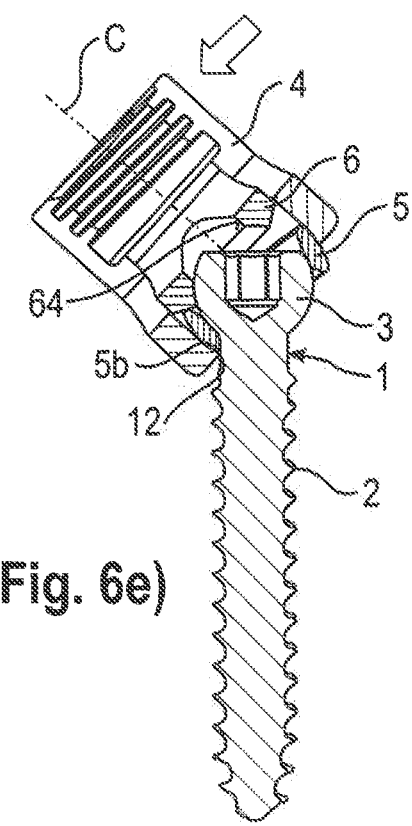
Fig. 6e)

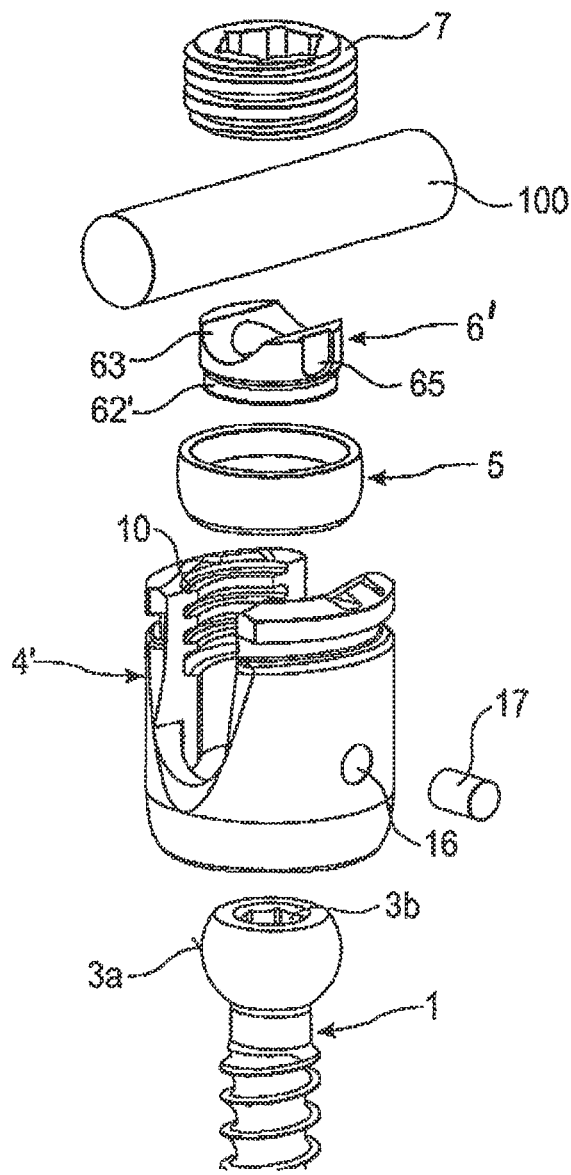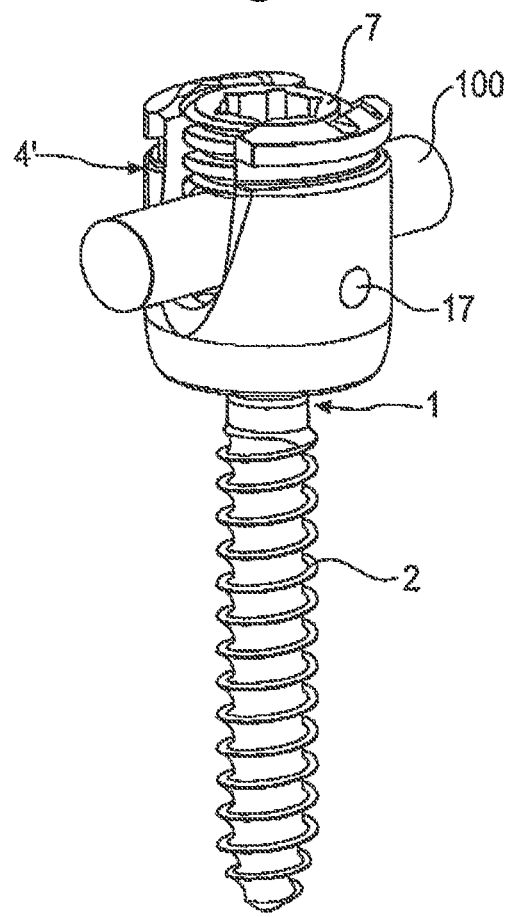

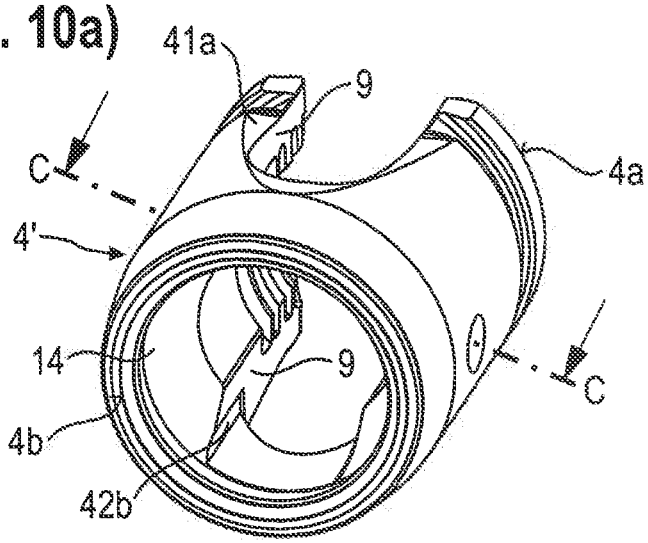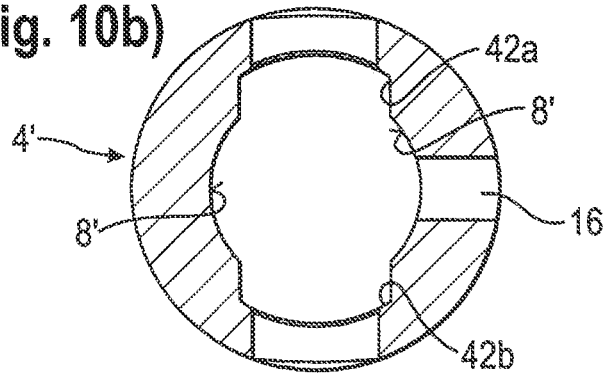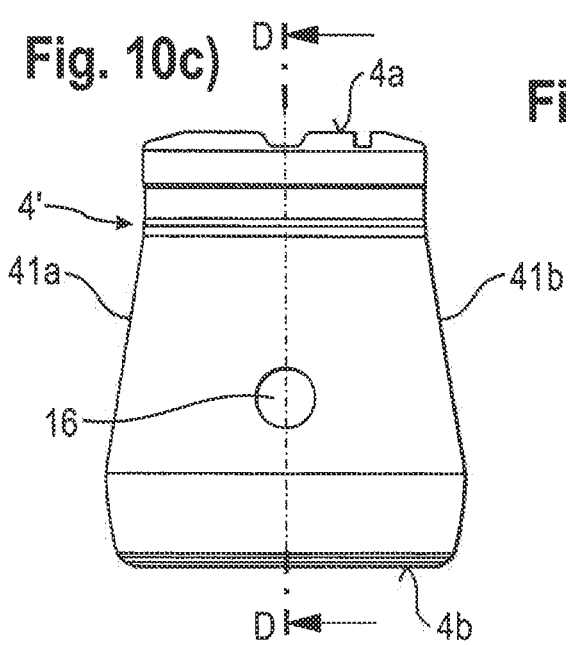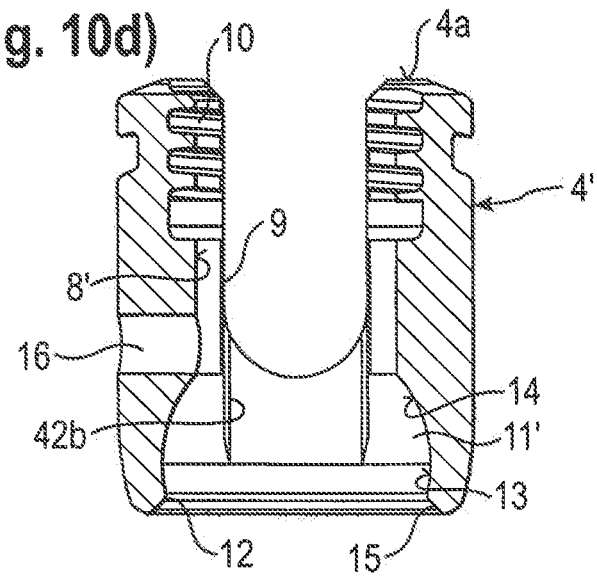

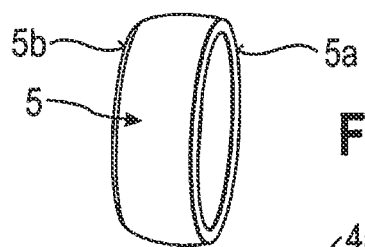
Fig. 11a)
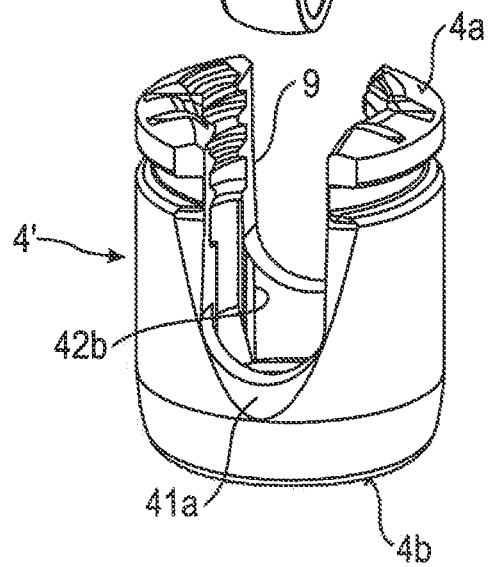
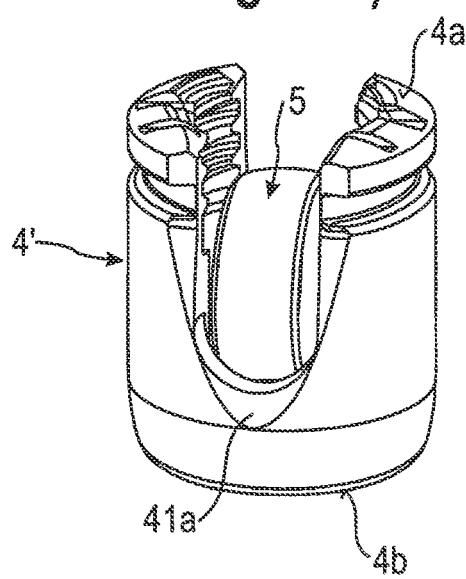
Fig. 11b)
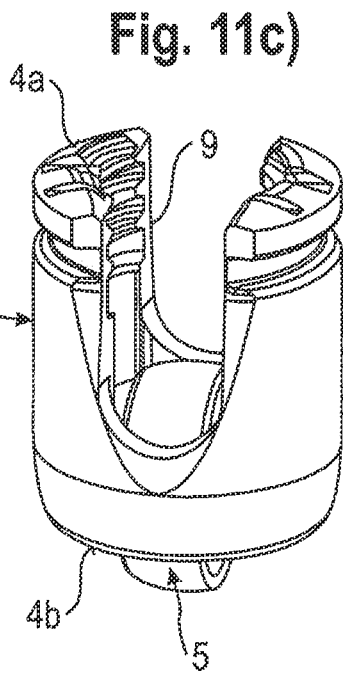
Fig. 11c)
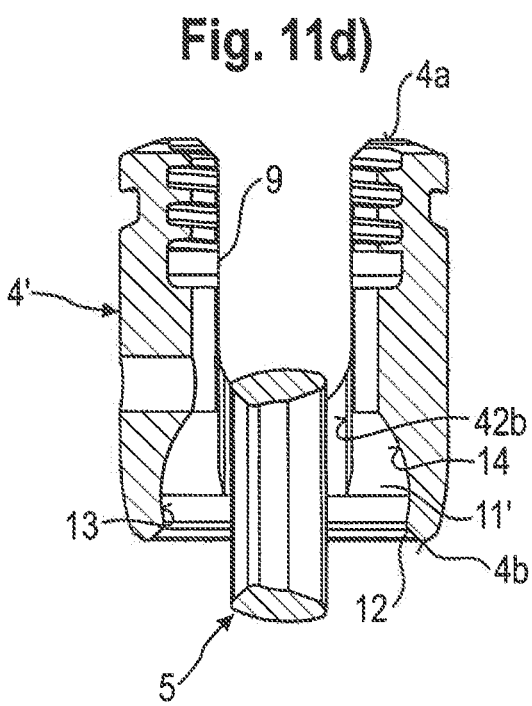
Fig. 11d)

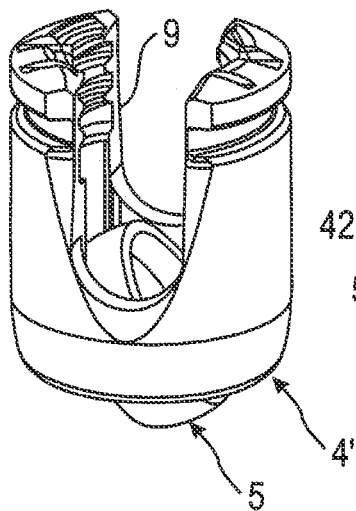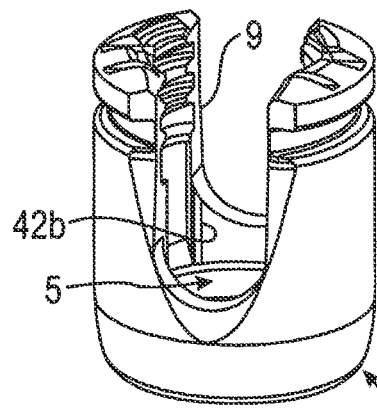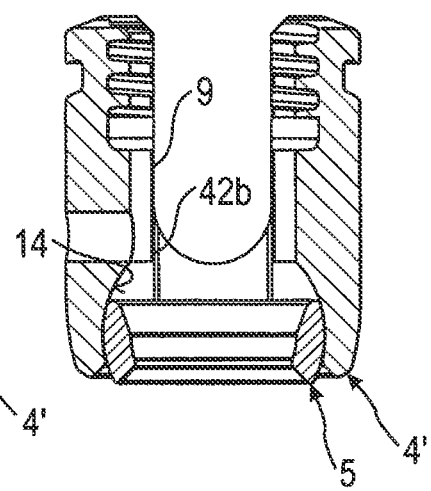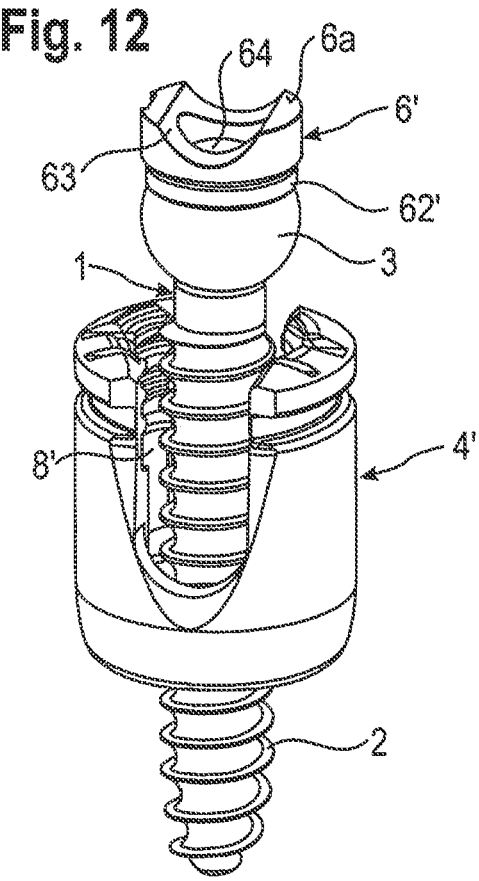

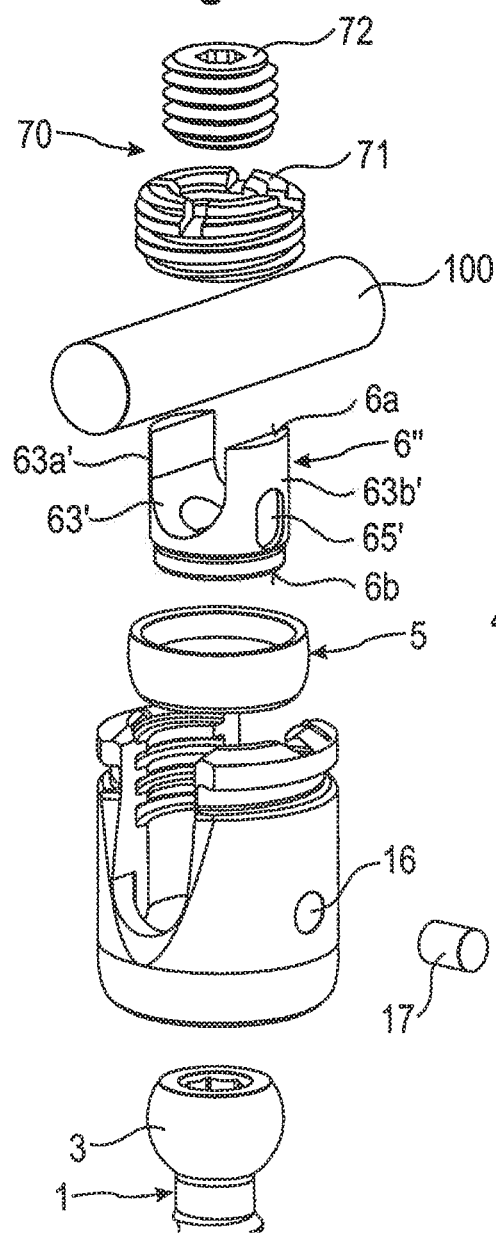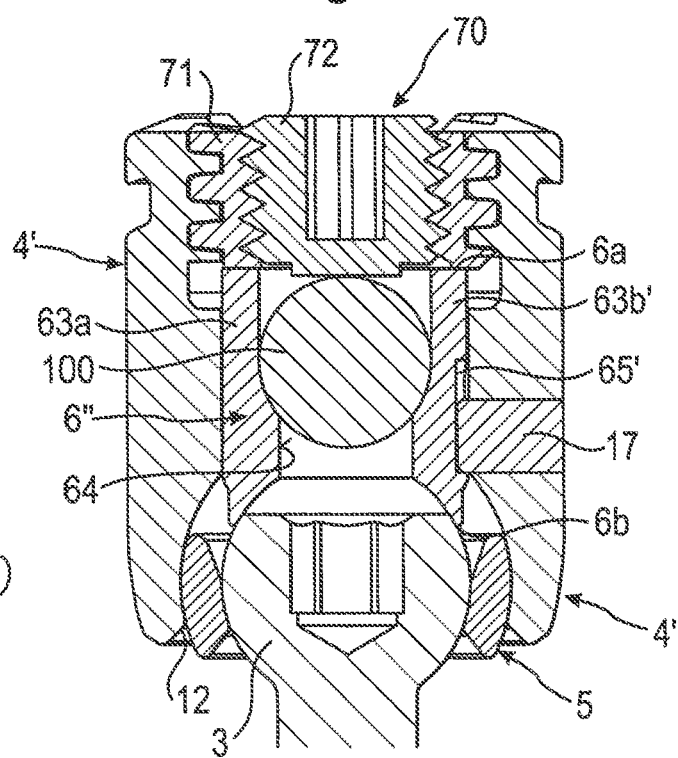

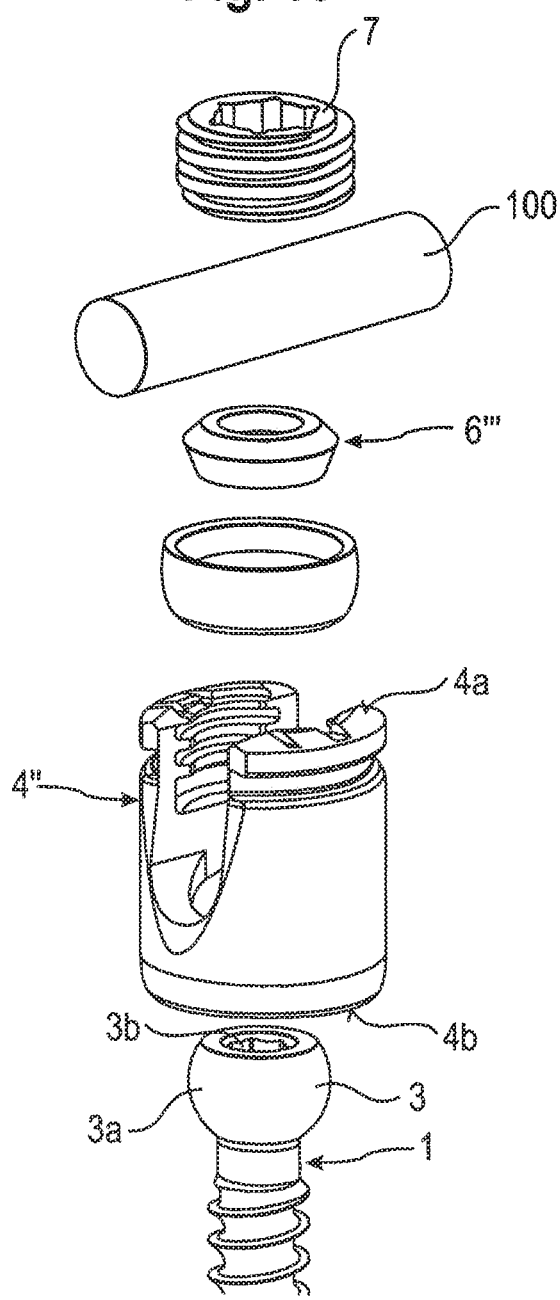
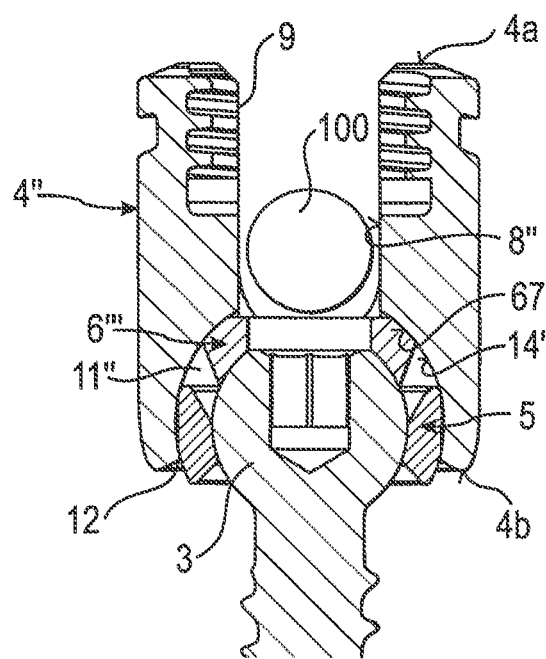

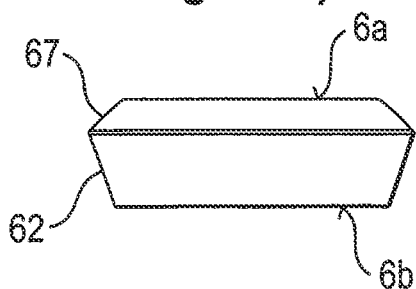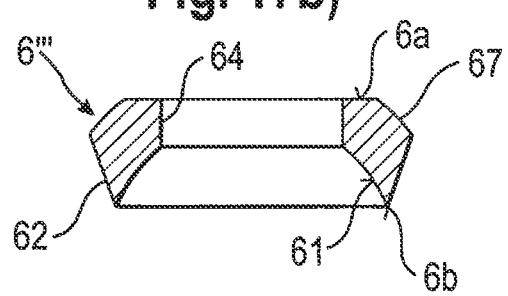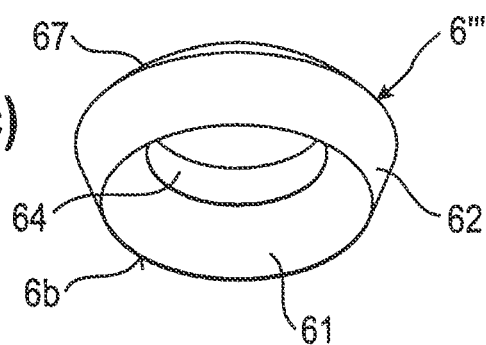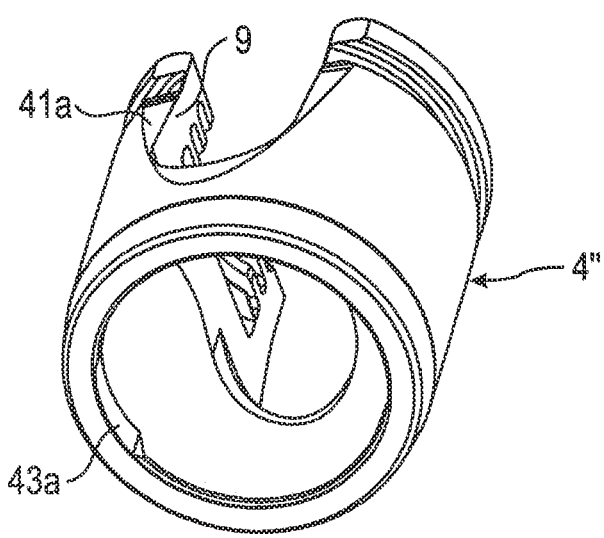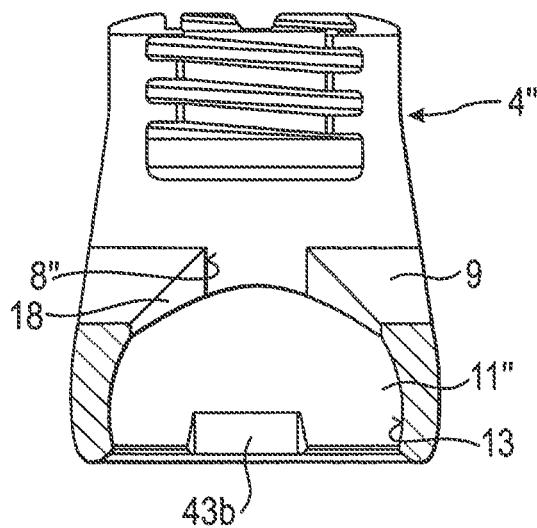

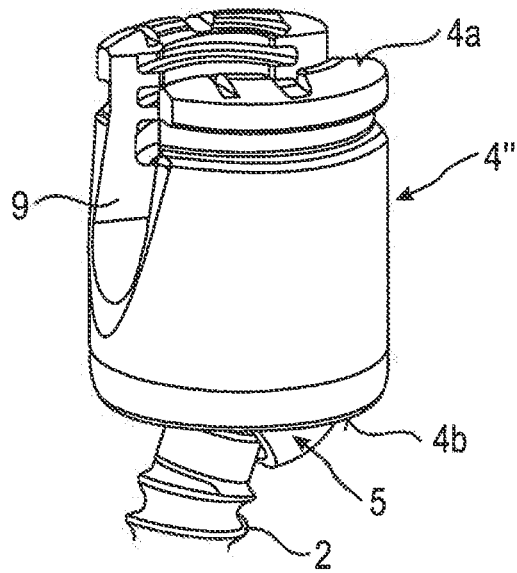
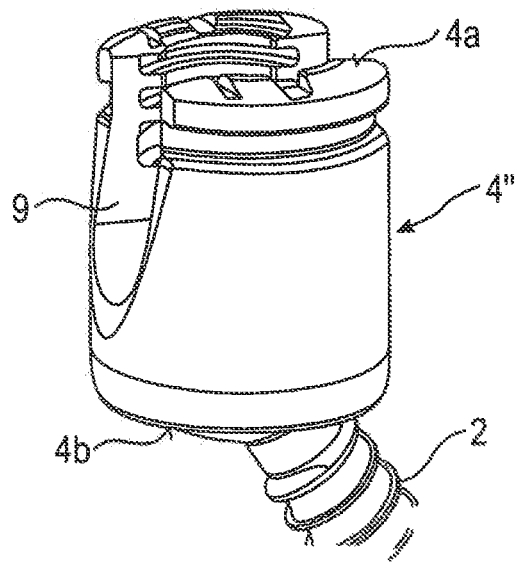
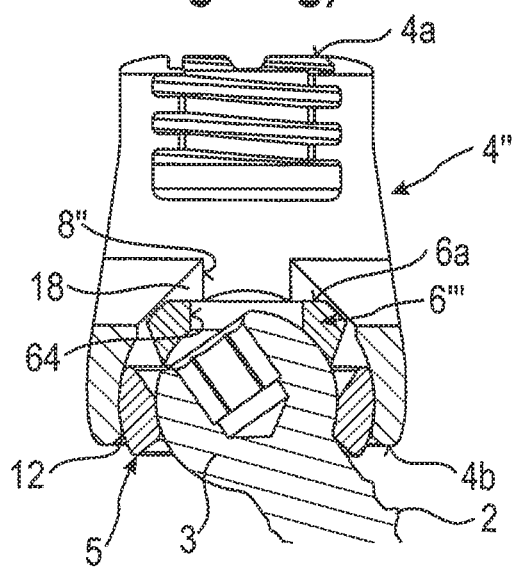
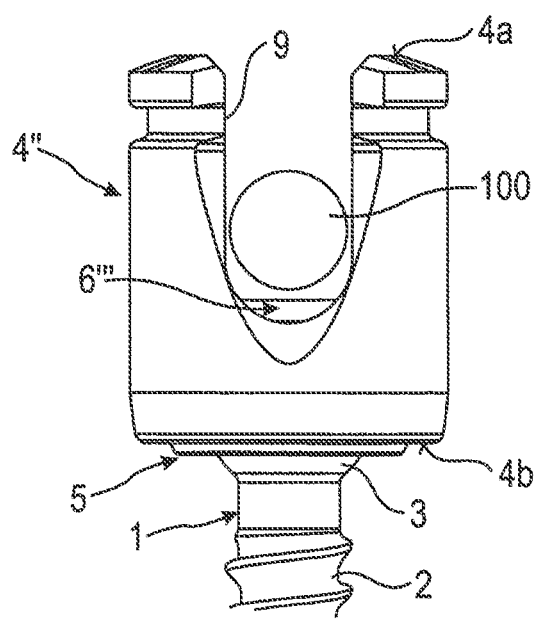

POLYAXIAL BONE ANCHORING DEVICE WITH ENLARGED PIVOT ANGLE

CROSS-REFERENCE TO RELATED APPLICATION(S)

This application is a continuation of U.S. patent application Ser. No. 16/259,373, filed Jan. 28, 2019, which is a continuation of U.S. patent application Ser. No. 15/676,795, filed Aug. 14, 2017, now U.S. Pat. No. 10,231,758, which is a continuation of U.S. patent application Ser. No. 13/304,228, filed Nov. 23, 2011, now U.S. Pat. No. 9,763,698, which claims priority to and the benefit of U.S. Provisional Patent Application Ser. No. 61/417,167, filed Nov. 24, 2010, the contents of each of which are hereby incorporated by reference in their entirety, and claims priority to European Patent Application EP 10 192 373.8, filed Nov. 24, 2010, the contents of which are hereby incorporated by reference in their entirety.

BACKGROUND

Field of the Invention

The invention relates to a polyaxial bone anchoring device with an enlarged pivot angle. The bone anchoring device includes a bone anchoring element for anchoring in a bone or a vertebra, and a receiving part for coupling the bone anchoring element to a stabilization element such as a spinal rod, where the bone anchoring element is pivotable in the receiving part and can be pivoted out of a central axis with an enlarged pivot angle. The orientation of the enlarged pivot angle may be selectable within a range of 360° around the central axis and may be automatically achieved by pivoting the receiving part relative to the bone anchoring element.

Description of Related Art

A polyaxial bone anchoring device with an enlarged pivot angle is described in U.S. Pat. No. 6,736,820. This bone anchoring device includes a bone screw and a receiving part with a seat for the head of the bone screw. In order that the screw member can be pivoted to at least one side by an enlarged angle, the edge bounding the free of the receiving part is of asymmetric construction. In a modified embodiment, an insert piece is provided, which has a spherical bottom as a seat for the head of the screw member.

US 2007/0118123 A1 describes a polyaxial bone anchor with increased angulation. The polyaxial bone anchor has a locking element shaped and configured to allow an anchoring member e.g. a screw or hook to polyaxially rotate at large angles about a central axis of the bone anchor before compression locking the anchoring member within an anchor head.

SUMMARY

Although the polyaxial bone anchoring devices described above provide for enlarged angulation in a desired orientation there is still a need for an improved polyaxial bone anchoring device in terms of, for example, simplicity of design.

It is an object of the invention to provide a polyaxial bone anchoring device that allows for adjustment of an orientation of an enlarged pivot angle, which has a simple design while also providing high efficiency of fixation.

A polyaxial bone anchoring device according to embodiments of the present invention has few parts and is of simple design. Therefore, the bone anchoring device is easy and cost effective to manufacture. It provides safe fixation, since a pressure to lock an angular position of a bone anchoring element with respect to a receiving part is applied effectively in an axial direction. The bone anchoring device may be devoid of any flexible parts or portions. Therefore it is reliable, even if during adjustment of the angular position the orientation of the enlarged pivot angle is changed several times.

A pivot angle of the bone anchoring element relative to the receiving part is equal to or greater than 45° measured from a straight position. This renders the bone anchoring device particularly suitable for the application of lateral mass fixation, for example, in the cervical spine.

The locking mechanism for locking the bone anchoring element and the sleeve-like insert piece provides for a high clamping force on a small surface. Therefore, the locking mechanism is efficient.

Although in a lower part of the receiving part an insert member is arranged which needs space for placement, an upper portion of the receiving part can be designed to be small in size.

The bone anchoring device can be designed as a top loading device, where the bone anchoring element is inserted from the top, or a bottom loading device where the bone anchoring element is inserted from the bottom.

BRIEF DESCRIPTION OF THE DRAWINGS

Further features and advantages of the invention will become apparent from the description of exemplary embodiments by means of the accompanying drawings. In the drawings:

FIG. 1 shows a perspective exploded view of a polyaxial bone anchoring device with a spinal rod according to a first embodiment;

FIG. 2 shows a perspective view of the bone anchoring device of FIG. 1 in an assembled state.

FIG. 3 shows a cross-sectional view of the bone anchoring device of FIGS. 1 and 2 in the assembled state without the rod or a fixation screw, the section being taken along a rod axis;

FIG. 4a shows a side view of a pressure element of FIG. 1;

FIG. 4b shows a cross-sectional view of the pressure element of FIG. 4a, the section being taken along line A-A in FIG. 4a;

FIG. 4c shows a bottom view of the pressure element of FIG. 4a;

FIG. 4d shows a perspective view of the pressure element of FIG. 4a;

FIG. 5a shows a side view of a sleeve-like insert piece of FIG. 1;

FIG. 5b shows a perspective view of the sleeve-like insert piece of FIG. 5a;

FIG. 5c shows a cross-sectional view of the sleeve-like insert piece of FIG. 5a along line B-B in FIG. 5a;

FIG. 5d shows an enlarged cross-sectional view of a portion of the insert piece shown in FIG. 5c;

FIGS. 6a to 6e show steps of aligning a polyaxial bone anchoring device according to an exemplary embodiment, with regard to orientation of an enlarged pivot angle;

FIG. 7 shows an exploded perspective view of a polyaxial bone anchoring device according to a second embodiment.

FIG. 8 shows a perspective view of the bone anchoring device of FIG. 7 in an assembled state;

FIG. 10a shows a perspective view from below the receiving part of the bone anchoring device according to the second embodiment;

FIG. 10b shows a cross-sectional view of the receiving part of FIG. 10a, the section being taken along line C-C in FIG. 10a;

FIG. 10c shows a side view of the receiving part of FIG. 10a;

FIG. 10d shows a cross-sectional view of the receiving part of FIG. 10c, the section being taken along line D-D in FIG. 10c;

FIGS. 11a to 11g show steps of assembling a sleeve-like insert piece and the receiving part according to an exemplary embodiment;

FIG. 12 shows a perspective view of assembling a receiving part with a sleeve-like insert piece and a bone anchoring element with a pressure element according to an exemplary embodiment;

FIG. 13 shows a perspective exploded view of a polyaxial bone anchoring device according to a modified embodiment;

FIG. 14 shows a cross-sectional view of the polyaxial bone anchoring device of FIG. 13 in an assembled state;

FIG. 15 shows a perspective exploded view of a third embodiment of a polyaxial bone anchoring device;

FIG. 16 shows a cross-sectional view of the polyaxial bone anchoring device of FIG. 15 in an assembled state, with a rod but without a fixation device, the section being taken perpendicular to a rod axis;

FIGS. 17a to 17c show different views of a pressure member of the polyaxial bone anchoring device of FIGS. 15 and 16;

FIGS. 18a to 18b show different views of a receiving part of the polyaxial bone anchoring device of FIGS. 15 and 16;

FIGS. 19a to 19g show steps of assembling the polyaxial bone anchoring device of FIGS. 15 and 16 in different views; and FIG. 20 shows a side view of a step of use of a polyaxial bone anchoring device after assembly.

DETAILED DESCRIPTION

Figure 9A:
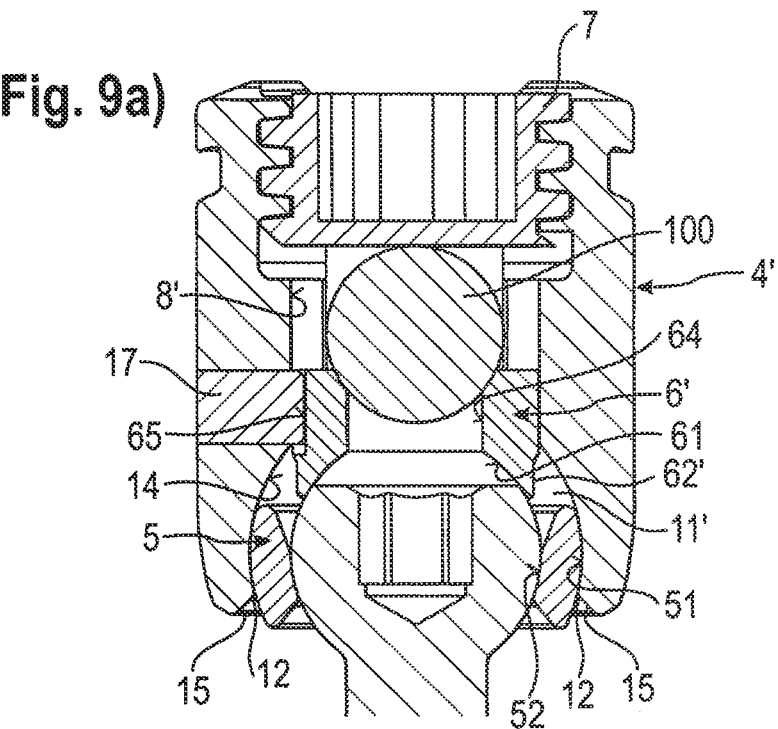
FIG. 9a shows a cross-sectional view of the polyaxial bone anchoring device of FIGS. 7 and 8 in an assembled state, the section being taken perpendicular to a rod axis, wherein a bone anchoring element assumes a first position with respect to a receiving part.

As shown in FIGS. 1 to 3, a polyaxial bone anchoring device according to a first embodiment includes a bone anchoring element 1 in the form of a bone screw having a threaded shaft 2 and a head 3. The head 3 typically has a spherically-shaped outer surface portion 3a and a recess 3b at its free end for engagement with a driver or tool. The head 3 may be held in a receiving part 4 that couples the bone anchoring element 1 to a stabilization rod 100. In the receiving part 4, a sleeve-like insert piece 5 providing a seat for the head 3 and a pressure member 6 for exerting pressure onto the head 3 are arranged. Furthermore, a fixation element in the form of, for example, fixation screw 7 is provided for securing and fixing the rod 100 in the receiving part 4.

The receiving part 4 has a top end 4a and a bottom end 4b, a central axis C and a coaxial bore 8 extending from the top end 4a in the direction of the bottom end 4b. Adjacent to the top end 4a, a substantially U-shaped recess 9 is provided that forms a channel for receiving the rod 100. By means of the recess 9, two free legs are formed which are provided with an internal thread 10 for cooperating with the fixation screw 7.

The coaxial bore 8 opens into an accommodation space 11 provided in a lower part of the receiving part 4 (e.g., nearer to the bottom end 4b). The accommodation space 11 has a lower opening 12 at the bottom end 4b of the receiving part 4. The accommodation space 11 further includes a seat portion 13 near the bottom end 4b of the receiving part 4 in which the sleeve-like insert piece 5 may be seated. The seat portion 13 has a spherical shape, in order to provide a socket for a ball and socket joint that is formed by the sleeve-like insert piece 5 and the receiving part 4. It should be noted that the seat portion 13 can also be tapered, or can have various other shapes that can be used to realize a ball and socket joint. An inner diameter of the lower opening 12 is smaller than an inner diameter of other portions of the accommodation space 11. It shall also be noted that an inner diameter of the coaxial bore 8 does not need to be constant between the top end 4a and the accommodation space 11. The coaxial bore 8 may have different portions with different diameters.

The sleeve-like insert piece 5 is shown in particular in FIGS. 3 and 5a to 5d. The sleeve-like insert piece 5 has an upper edge 5a and a lower edge 5b. Between the upper edge 5a and the lower edge 5b the sleeve-like insert piece 5 may have a spherically-shaped outer surface portion 51. A largest outer diameter of the sleeve-like insert piece is greater than the inner diameter of the lower opening 12 of the receiving part 4. Hence, the sleeve-like insert piece 5 cannot escape through the lower opening 12 when it is seated in the receiving part 4. The dimension or shape of the outer spherical surface portion 51 corresponds to that of the spherically-shaped seat portion 13 in the receiving part 4 in such a way that the sleeve-like insert piece 5 can pivot and rotate in the receiving part 4 when the insert piece 5 is seated in the seat portion 13. When the sleeve-like insert piece 5 rests in the seat portion 13, such that its center axis 5c is coaxial with the center axis C of the receiving part 4, the lower edge 5b projects out of the lower opening 12. When the sleeve-like insert piece 5 is pivoted or angled in the receiving part, as shown for example, in FIG. 3, at least a portion of the lower edge 5b still projects out of the lower opening 12.

The sleeve-like insert piece 5 is hollow and has a central portion 52 that is spherically-shaped with a radius corresponding to a radius of the spherically-shaped outer surface portion 3a of the head 3 of the bone anchoring element 1. A lower end of the central portion 52 forms a shoulder 53. An inner diameter of the shoulder 53 is smaller than a largest outer diameter of the spherical head 3, so that the head 3 can rotate and pivot in the central spherical portion 52 of the sleeve-like insert piece 5, similar to a ball and socket joint. Between the shoulder 53 and the lower edge 5b, a tapered portion 54 is provided that tapers outward to allow angulation of the bone anchoring element 1 until the shaft 2 comes into contact with the lower edge 5b. Between the spherical central portion 52 and the upper edge 5a, a tapered portion 55 is provided which also tapers outward. An inner diameter of the tapered portion 55 and of a transition between the tapered portion 55 and the spherical central portion 52 are greater than the largest outer diameter of the head 3, so that the head 3 can be inserted from the upper edge 5a. At an upper edge 5a, a chamfered portion 56 is provided that may serve as a stop for the pressure member 6.

Center points of the spherical central portion 52 and the outer spherical portion 51 may be offset in such a way that the center point of the inner central spherical portion 52 is shifted in the direction towards the bottom end 4b or the lower edge 5b, relative to the center point of the outer spherical portion 51. By means of this, a range of angulation of the bone anchoring element 1 can be further increased. A height of the sleeve-like insert piece 5 in axial direction is less than a height of the head 3 in an axial direction, such that when the head 3 is inserted into the sleeve-like insert piece 5, a portion of the spherical outer surface 3a of the head 3 still projects from the upper edge 5a of the sleeve-like insert piece 5.

The pressure member 6 is shown in particular in FIGS. 1, 3, and 4a to 4d. The pressure member 6 is substantially cylindrical with an outer diameter that allows it to move within the coaxial bore 8 and the accommodation space 11. The pressure member 6 has an upper end 6a and a lower edge 6b. Adjacent its lower edge 6b, the pressure member 6 has a spherical recess 61 with a spherical shape that matches the spherical shape of the outer spherical surface portion 3a of the head 3. Adjacent the lower edge 6b, there is a tapered portion 62 that can abut against the chamfered portion 56 of the sleeve-like insert piece 5. At the upper end 6a, the pressure member 6 has a cylindrical recess 63 for receiving the rod 100 therein. Furthermore, pressure member 6 has a coaxial bore 64 for allowing access to the screw head 3 by a tool. The coaxial bore 64 is also configured to allow a portion of the head 3 to extend therethrough when the bone anchoring element is in a pivoted condition, for example, as shown in FIG. 3. A height of the pressure member 6 in an axial direction is such that when the fixation screw 7 is tightened, the fixation screw 7 presses onto the upper end 6a of the pressure member 6, while the pressure member 6 acts onto the head 3 of the bone anchoring element 1.

The bone anchoring device according to the first embodiment may be pre-assembled in such a way that the sleeve-like insert piece 5, the head 3 of the bone anchoring element 1 and the pressure member 6 are arranged in the receiving part 4. For assembling the bone anchoring device, the sleeve-like insert piece 5, the bone anchoring element 1 and the pressure member 6 may all be inserted through the top end 4a. The pressure member 6 is arranged in an aligned position in which the cylindrical recess 63 is aligned with the U-shaped recess 9 of the receiving part for receiving the rod 100. The pressure member 6 may be held provisionally in this position, for example, by crimping.

The bone anchoring device, as a whole or in parts, is made of a bio-compatible material, such as a bio-compatible metal, for example titanium or stainless steel, a bio-compatible alloy, such as Nitinol, or of bio-compatible plastic materials, such as, for example, polyetheretherketone (PEEK).

The steps of use, for example, for adjusting between different positions of the bone anchoring device according to the first embodiment are shown in FIGS. 6a to 6e. First, the bone anchoring element 1 is inserted in the bone part or in a vertebra that is to be stabilized. Usually several bone anchoring devices are needed to fix a stabilization rod to the bone parts or vertebrae to be stabilized. After the bone anchoring elements 1 are inserted, one example of which is shown in FIG. 6a, the receiving part 4 is adjusted by pivoting and/or rotating the receiving part 4 into a position to be able to take up or receive the stabilization rod 100.

In the conditions shown in the FIGS. 6a to 6e, the sleeve-like insert piece 5 and the head 3 of the bone anchoring element 1 are independently and freely pivotable. The sleeve-like insert piece 5 is rotatable and pivotable in the receiving part 4, while the receiving part 4 and the sleeve-like insert piece 5 are rotatable and pivotable with respect to the head 3 of the bone anchoring element 1. The sleeve-like insert piece 5 provides for an enlarged range of angulation compared to bone anchoring devices where the head 3 is directly received in the receiving part 4, because the insert piece 5 projects out of the lower opening 12, thereby enlarging or increasing a distance between the shaft 2 of the bone anchoring element 1 and the abutment provided by the edge of the lower opening 12. Since the sleeve-like insert piece 5 is rotatable and pivotable within the receiving part 4, the enlarged range of angulation can be achieved at any position of the receiving part 4 with respect to the bone anchoring element 1, for all 360° around the central axis C of the receiving part 4. As shown in FIG. 6b, pivoting of the receiving part 4 with respect to the bone anchoring element 1 may initially essentially or substantially maintains a position of the sleeve-like insert piece 5 relative to the receiving part 4. When the shaft 2 of the bone anchoring element 1 comes into contact with the lower edge 5b of the sleeve-like insert piece, as shown in FIG. 6c and in the enlarged portion according to FIG. 6d, the sleeve-like insert piece 5 is also pivoted with the bone anchoring element 1. The shaft 2 may push the insert piece 5 until the shaft 2 abuts against the edge of the lower opening 12 of the receiving part 4, as shown in FIG. 6e. Hence, in FIG. 6e, the receiving part 4 is pivoted at a maximum pivot angle with respect to the bone anchoring element 1. The maximum pivot angle that can be achieved depends on the dimensions of the sleeve-like insert piece 5, the receiving part 4, and the bone anchoring element 1, but is typically equal to or greater than 45° measured from a straight or zero angle position between the receiving part 4 and the bone anchoring element 1.

While in FIGS. 6a to 6e, an example is shown in which pivoting is carried out in a plane that contains the rod axis, it should be noted that the same steps can be carried out at, for example, 90° to the plane containing the rod axis, or at any other directions within 360° around the central axis C of the receiving part 4.

Finally, the rod is inserted, and the inner screw 7 is tightened to press the pressure member 6 onto the head 3 to lock the head 3 and the sleeve-like insert piece 5 simultaneously.

FIGS. 7 to 12 show a second embodiment of the bone anchoring device. Parts and portions which are the same or similar to those of the first embodiment are designated with the same reference numerals, and the descriptions thereof are not repeated. The bone anchoring device of the second embodiment differs from the bone anchoring device of the first embodiment by the construction of the receiving part and the pressure member. All other parts may be identical or similar to those of the first embodiment.

The presence of the sleeve-like insert piece 5 may have the consequence that in order to have the space for the insert piece 5, a lower portion of the receiving part may have an increased outer diameter when compared to receiving parts which do not include such an insert piece. There is, however, a need that at a location for a rod, the receiving part has a small or smaller size. A receiving part 4' according to the second embodiment may have a smaller outer diameter at an upper portion which takes up or receives a rod when compared to the receiving part of the first embodiment, as can be seen in particular in FIGS. 7, 8, and 10. The receiving part 4' has two tapered outer surface portions 41a, 41b which taper towards the top end 4a to reduce the size of the receiving part 4'. The tapered outer surface portions 41a, 41b are located 180° offset from each other, and may be transverse to a longitudinal axis of the rod 100 which corresponds to a longitudinal axis of the U-shaped recess 9. Therefore, the dimensions of the receiving part 4' in the direction of the rod axis is reduced compared to that of the first embodiment. In order to have sufficient wall strength, the coaxial bore 8' may have a smaller diameter compared to the coaxial bore 8 of the first embodiment. The diameter of the coaxial bore 8' may be smaller than the largest outer diameter of the sleeve-like insert piece 5. The coaxial bore 8' opens toward an accommodation space 11'. The accommodation space 11' has the seat portion 13 and a lower opening 12, similarly as seen in the first embodiment. Further, the accommodation space 11' has a dome-shaped portion 14 between the seat portion 13 and the coaxial bore 8'. The dome-shaped portion 14 and/or the seat portion 13 define a largest inner diameter of the accommodation space 11', which is larger than the inner diameter of the coaxial bore 8'. Further, the receiving part 4' may have an outwardly tapering portion 15 tapering outwards from the opening 12 to further increase a range of angulation of the bone anchoring element 1. The size of the accommodation space 11' is such that the sleeve-like insert piece 5 can be tilted therein when the insert piece 5 is introduced from the top end 4a in a tilted position, as will be explained below.

In order to allow the sleeve-like insert piece 5 to be introduced from the top end 4a, two opposed recesses 42a, 42b are provided in the inner wall of the coaxial bore 8' and the accommodation space 11'. The recesses 42a, 42b are aligned with the U-shaped recess 9. The recesses 42a, 42b extend from a bottom of the U-shaped recess 9 into the accommodation space 11'.

The size of the recesses 42a, 42b are such that the sleeve-like insert piece 5 can be introduced from the top end 4a in a 90° tilted position, i.e. the width of the recesses 42a, 42b are greater than the height of the sleeve-like insert piece 5 in its axial direction. The recesses 42a, 42b extend into the accommodation space 11' to such an extent that tilting of the insert piece 5 into the seat 13 is possible.

Furthermore, the receiving part has at least one pin hole 16 for receiving a pin 17 as shown in FIGS. 7 to 10. The pin hole 16 may be arranged at 90° relative to the channel axis. A second pin (not shown) may be provided on, for example, an opposite side of the receiving part. However, it is not necessary to provide a second pin.

Figure 9B:
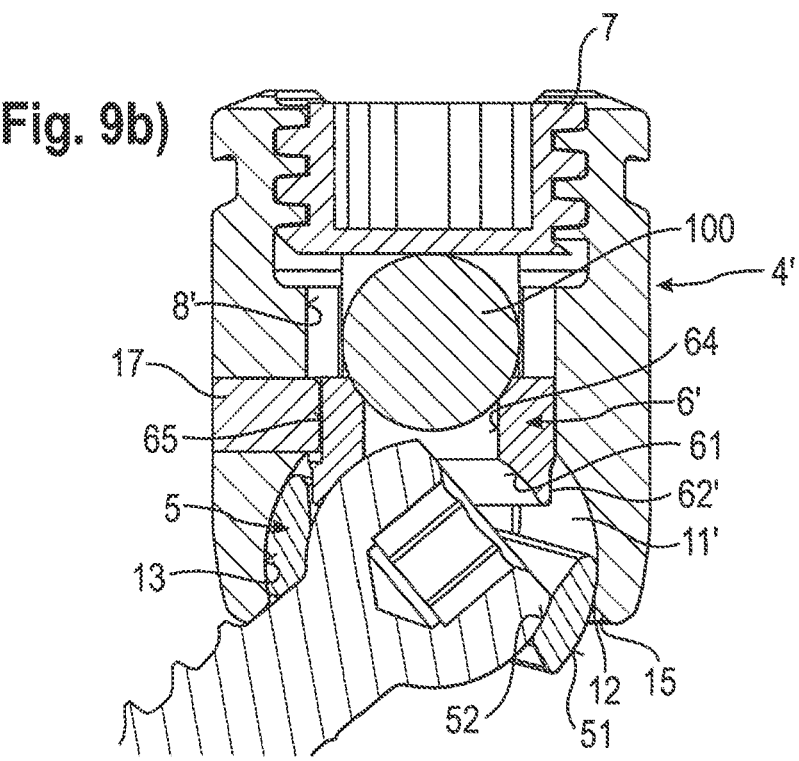
FIG. 9b shows a cross-sectional view of the bone anchoring device of FIGS. 7 and 8 in the assembled state, wherein the bone anchoring element assumes a second position with respect to the receiving part.

As shown in FIGS. 7, 9a and 9b, the pressure member 6' differs from the pressure member 6 in that it has, instead of a tapered portion 62, a cylindrical portion 62' with a diameter which is slightly smaller than a diameter of a cylindrical main portion of the pressure member 6'. The outer diameter of the lower cylindrical portion 62' is smaller than an inner diameter of the upper tapered portion 55 of the sleeve-like insert piece 5, so that the lower cylindrical portion 62' can be arranged at least partially within the upper tapered portion 55 of the sleeve-like insert piece 5. By means of this, the pressure member 6' may not touch the sleeve-like insert piece 5.

The pressure member 6' has on one side, perpendicular to a cylinder axis of cylindrical recess 63, a coaxial recess 65 in its outer wall which is closed towards a lower edge 6b and open towards an upper end 6a (see, e.g., FIG. 4a). A bottom of the recess 65 towards the lower edge 6b may be rounded. The recess 65 serves for receiving the pin 17, which holds the receiving part in an aligned position, so that the cylinder axis of cylindrical recess 63 and a channel axis of the U-shaped recess are aligned to receive the rod 100. The recess 65 and the pin 17 form a device or engagement for preventing rotating and escaping of the pressure member 6' from the receiving part 4'.

The position and dimension of the pin hole 16, the pin 17, and the recess 65 may be configured such that the pressure member 6' is provisionally fixed to exert a slight preload onto the head 3. By means of this the head 3 is clamped by friction before it is finally locked by tightening the fixation screw 7 and pressing down the pressure member 6'. Hence, the receiving part 4' can be held in an adjustable angular position with respect to the bone anchoring element. Pivoting the receiving part 4' with respect to the bone anchoring element 1 in this configuration is still possible by applying a force that is greater than the friction force.

The steps of assembling the bone anchoring device according to the second embodiment are shown with respect to FIGS. 11a to 11g. First, as can be seen in FIGS. 11a and 11b the sleeve-like insert piece 5 is tilted by 90° and inserted in the receiving part 4' at the position of the U-shaped recess 9. Then, as shown in FIGS. 11c and 11d, where FIG. 11d is a cross-sectional view of FIG. 11c, the insert piece 5 is moved downward into the accommodation space 11'. Since the outer diameter of the insert piece 5 is larger than the inner diameter the lower opening 12, the insert piece cannot escape through the lower edge of the opening 12. Then, as shown in FIGS. 11e to 11g, where FIG. 11g is a cross-sectional view of the receiving part 4' according to FIG. 11f, the insert piece 5 is titled so that it is seated in the seat portion 13. Thereafter, the bone anchoring element 1, which may also include the pressure member 6' on top of head 3, is inserted from the top end 4a. Thereafter, the pressure member 6' is held by introducing the pin 17 into the pin hole 16 until it engages the recess 65.

Use of the bone anchoring device of the second embodiment is similar to that of the first embodiment.

FIGS. 13 and 14 show a modification of the second embodiment. All parts which are identical or similar to those of the second embodiment are designated with the same reference numerals, and the descriptions thereof are not repeated.

The modified second embodiment differs from the second embodiment by the design of the pressure member 16" and of the fixation device 70. The bone anchoring device has separate head and rod fixation mechanisms. This is achieved by the pressure member 6" being taller in an axial direction, such that, instead of the cylindrical recess 63, a U-shaped recess 63' is provided with legs 63a', 63b' that extend above the rod 100 when the rod 100 is inserted in the channel formed by the U-shaped recess 63'. Furthermore, the pressure member 6" may have an oblong recess 65' which is closed towards both the upper end 6a and the lower edge 6b.

The fixation device 70 is a two-part fixation device including an inner screw 71 cooperating with the internal thread 10 of the receiving part 4'. The inner screw 71 has a coaxial threaded hole for receiving a set screw 72. The set screw 72 acts upon the rod 100. When the inner screw 71 is tightened it presses onto the top end 6a of the pressure member 6" to exert pressure onto the head 3 of the bone anchoring element 1. With the set screw 72, the rod 100 can be fixed separately.

The assembly and use of the bone anchoring device according to the modified second embodiment is similar to that of the second embodiment. It shall be noted that similar fixation devices and modified pressure members can also be used in connection with the bone anchoring device of the first embodiment.

A third embodiment of the bone anchoring device is shown FIGS. 15 to 20. The third embodiment differs from the bone anchoring devices of the previous embodiments in that the sleeve-like insert piece 5 can be introduced from the bottom end 4*a* of the receiving part. Therefore, the third embodiment differs from the bone anchoring devices of the previous embodiment in that it can be categorized as a bottom loading polyaxial bone anchoring device, in which the bone anchoring element 1 can be introduced from a bottom end 4*b*. As in the previous embodiments, identical or similar features are designated by the same reference numerals and the descriptions thereof will not be repeated.

Figure 19A:
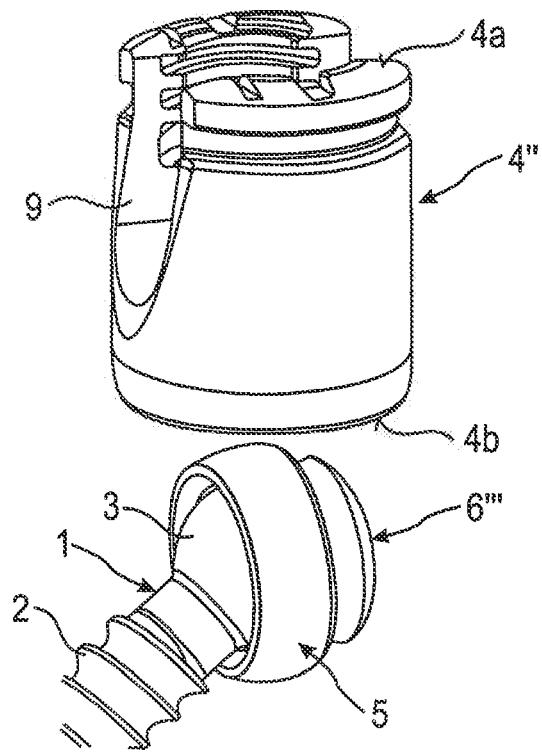

The polyaxial bone anchoring device according to the third embodiment has a receiving part 4" which is sized and shaped to receive the bone anchoring element 1, the sleeve-like insert piece 5, and the pressure member 6''' from the bottom end 4*b*. For this purpose, the receiving part 4" has at its bottom end two recesses 43*a*, 43*b*, which are offset by 180° from each other and which may be located at positions perpendicular to the rod axis. The recesses 43*a*, 43*b* are open to the bottom end 4*b*, and are sized and shaped such that the sleeve-like insert piece 5 can be introduced from the bottom end 4*b* into the accommodation space 11" in a 90° tilted position, for example, as shown in FIG. 19*a*. It should be noted that the recesses 43*a* and 43*b* need not necessarily be positioned at 90° with respect to the rod axis, but can be positioned also at 0° or at any other angle with respect to the rod axis. If they are located at 90° with respect to the rod axis, a weakening of the overall strength of the receiving part may be lower. The accommodation space 11" is substantially hollow and hemispherical, to allow the insertion of the head 3 with the sleeve-like insert piece and pressure member 6*m*. In other words, the accommodation space 11" is sized and shaped so as to allow introduction and rotation of the head 3 with the sleeve-like insert piece 5 and pressure member 6*m* mounted thereon. A lower portion of the coaxial bore 8" which opens into the accommodation space 11" has a portion 18 tapering outwards towards the bottom end 4*b*. This allows the head 3 with mounted sleeve-like insert piece 5 and pressure member 6''' to have space to be rotated in the accommodation space 11".

The coaxial bore 8" can have a smaller diameter compared to the coaxial bore 8 and 8' of the previous embodiments, since it is not necessary in this embodiment to guide the pressure member 6''' and/or the sleeve-like insert piece 5 through the coaxial bore 8". Therefore, the size of the receiving part 4" in an upper area can be reduced. A diameter of the coaxial bore 8" as shown in FIG. 16 is smaller than the largest outer diameter of the pressure member 6*m*. Therefore, it is not necessary to provide a provisional fixation of the pressure member 6''' to prevent escaping of the pressure member 6*m*.

The sleeve-like insert piece 5 of the third embodiment is substantially the same as the sleeve-like insert pieces 5 of the previous embodiments.

The pressure member 6*m*, as shown in FIGS. 17*a* to 17*c*, is a rotationally symmetric part having an upper end 6*a* and a lower edge 6*b*. Adjacent the lower edge 66, the pressure member 6''' has a spherically-shaped recess 61 similarly as seen in the previous embodiments. There is no cylindrical recess for receiving the rod 100, or in other words, the upper end 6*a* is a flat surface. Furthermore, the pressure member 6''' has a coaxial bore 64 for allowing access to the head 3 with a driver or tool, and for allowing the head 3 to extend partially therethrough when the bone anchoring element 1 is pivoted at large angles. Adjacent the lower edge 6*b*, an outer surface portion 62 is tapered as in the first embodiment. Adjacent the upper end 6*a*, there is a small spherically-shaped outer surface portion 67 which is sized and shaped to match with a dome-shaped portion 14' of the accommodation space 11', to facilitate rotation of the head 3 with the pressure element 6''' mounted thereon. The portion 67 may be small, for example, the portion 67 may only be a chamfered portion to facilitate rotating.

Figure 19B:
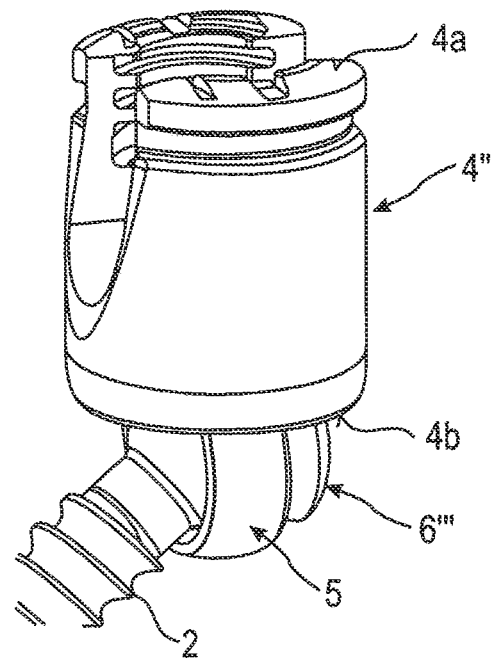
Figure 19C:
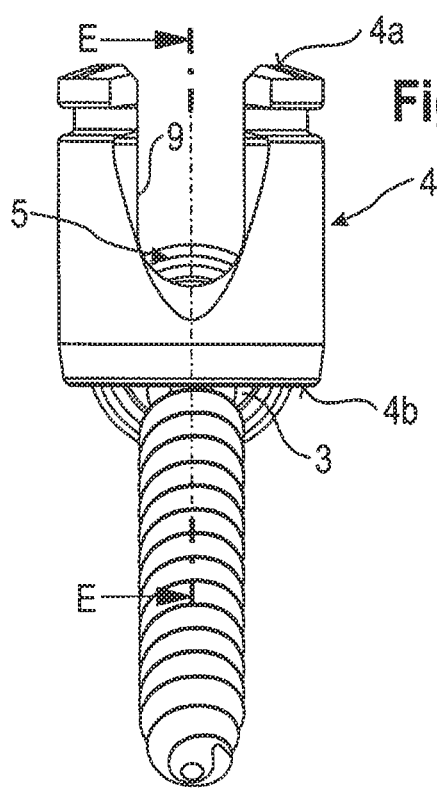
Figure 19D:
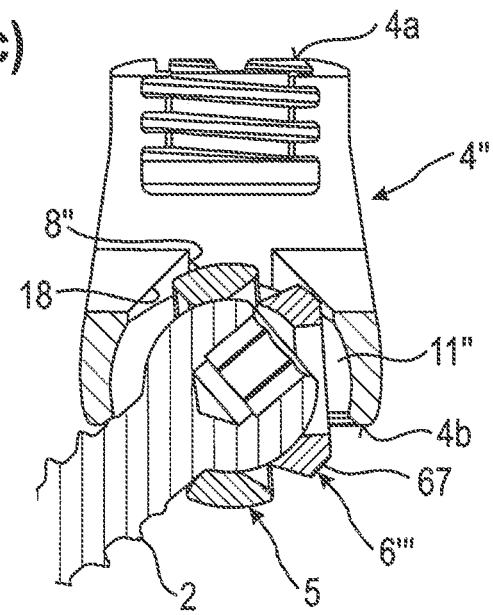

The assembly of the third embodiment will now be explained with respect to FIGS. 19*a* to 19*g*. FIG. 19*a* shows a side view of the receiving part 4" and the bone anchoring element before assembly. The bone anchoring element 1 is provided with the sleeve-like insert piece 5 and the pressure member 6*m*. The sleeve-like insert piece 5 and the pressure member 6''' are tilted so that their central axes are perpendicular to the central axis C of the receiving part 4". There may be a tool for holding the bone anchoring element 1 with the sleeve-like insert piece 5 and the pressure member 6*m* mounted thereon in such a position. Then, as shown in FIG. 19*b*, which is also a side view, the bone anchoring element 1 with the sleeve-like insert piece 5 and the pressure member 6*m* are introduced in this tilted position from the bottom end of the receiving part 4" through the lower opening 12 into the accommodation space 11". The receiving part 4" and the tilted sleeve-like insert piece 5 are oriented with respect to each other in such a manner that the sleeve-like insert piece 5 can be introduced at the position where the recesses 43*a*, 43*b* are provided in the receiving part 4". FIG. 19*c* shows a side view along a rod axis of the position shown in FIG. 19*b*. FIG. 19*d* shows sectional view along line E-E in FIG. 19*c*. As can be seen in FIG. 19*d* upon further insertion from the bottom end, the sleeve-like insert piece 5 may extend partially into the coaxial bore 8" and the tapering portion 18 in this position.

Next, as shown in FIGS. 19*e* and 19*f* which are side views of the bone anchoring device, the sleeve-like insert piece 5 and the pressure member 6" are rotated within the accommodation space 11" by pivoting the bone anchoring element 1. When the shaft 2 of the bone anchoring element 1 abuts against a lower edge 5*b* of the sleeve-like insert piece 5, the sleeve-like insert piece 5 pivots with the bone anchoring element 1. Simultaneously, the pressure member 6*m* may be guided along the wall of the accommodation space 11". Finally, as shown in the sectional view according to FIG. 19*g* the sleeve-like insert piece 5 and the pressure member 6*m* are in a zero-angle position, or in other words, their central axes are coaxial with the central axis C of the receiving part 4".

When the polyaxial bone anchoring device is assembled, the pressure member 6" projects slightly over the bottom of the U-shaped recess 9. When the rod 100 is inserted, it touches the upper flat surface 6*a* of the pressure member 6*m*. Tightening of an inner screw 7 or another fixation device presses the rod 100 against the pressure member 6''', which in turn presses onto the head 3 of the bone anchoring device, to simultaneously lock the angular position of the head 3 within the sleeve-like insert piece 5 and of the sleeve-like insert piece 5 within the receiving part 4".

Further modifications of the embodiments described may also be made. For example, for the bone anchoring element, various different kinds of anchoring elements can be used and combined with the receiving part. These anchoring elements may be, for example, screws with different length, screws with different diameters, cannulated screws, screws with different thread forms, nails, hooks, etc. For some anchoring elements, the head and the shaft may also be separate parts that are connectable to each other.

Other possible modifications of the receiving part may include, for example, instead of the U-shaped recess being perpendicular to the central axis, a recess for the rod may be inclined, open to the side, or in the form of a closed channel. Other kinds of locking devices including outer nuts, outer caps, bayonet locking devices, or others are also possible. In some embodiments, the inner surface portion of the pressure member that contacts the head 3 may not necessarily be spherically-shaped. The inner surface portion may have any other shape that is suitable to exert pressure onto the head.

It shall also be noted that portions of the different described embodiments can also be combined with each other in various different combinations.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising:
   an anchoring element having a shaft for anchoring in a bone and a head, the head comprising a spherically-shaped outer surface portion;
   a receiving part configured to be pivotably connected to the head, the receiving part having a top end and a bottom end, a longitudinal axis extending through the top end and the bottom end, a channel transverse to the longitudinal axis for receiving a rod, and an accommodation space for accommodating the head;
   a sleeve-like insert piece configured to pivot in the receiving part, the insert piece having a top end and a bottom end, and comprising a spherically-shaped exterior surface portion, a spherically-shaped seat configured to hold the head, and an inner tapered portion that widens as the inner tapered portion extends from the seat towards the top end of the insert piece; and
   a pressure member positionable at least partially in the accommodation space;
   wherein when the head, the insert piece, and the pressure member are in the receiving part and the head is held in the seat, the insert piece is tiltable with respect to the longitudinal axis of the anchoring element and with respect to a longitudinal axis of the receiving part to a position where the inner tapered portion directly contacts the pressure member, and the anchoring element is tiltable to substantially the same maximum pivot angle in every radial direction relative to the longitudinal axis of the receiving part while a rotational orientation of the insert piece relative to the receiving part remains constant; and
   wherein the anchoring element and the insert piece are configured to be locked at respective angles relative to the longitudinal axis of the receiving part when the pressure member directly contacts the head and exerts pressure onto the head.

2. The polyaxial bone anchoring device of claim 1, wherein the insert piece and the anchoring element are independently moveable when arranged in the receiving part when the shaft of the anchoring element and the bottom end of the insert piece are not in contact with one another.

3. The polyaxial bone anchoring device of claim 1, wherein when the shaft of the anchoring element is pivoted in a first radial direction and engages the bottom end of the insert piece, further pivoting of the anchoring element in the same direction causes the insert piece to pivot together with the anchoring element.

4. The polyaxial bone anchoring device of claim 1, wherein when the pressure member is in contact with the head in the receiving part, the pressure member and the insert piece are configured to be completely spaced apart from one another.

5. The polyaxial bone anchoring device of claim 1, wherein the pressure member is configured to be held in the receiving part in a position such that the pressure member exerts a preload onto the head, which clamps the head by friction before a final locking of an angular position of the anchoring element.

6. The polyaxial bone anchoring device of claim 1, wherein the pressure member has a recess configured to receive the rod.

7. The polyaxial bone anchoring device of claim 1, wherein the bottom end of the insert piece extends past the bottom end of the receiving part in a direction away from the top end of the receiving part when the insert piece is seated in the receiving part and a central axis of the insert piece is coaxial with the longitudinal axis.

8. The polyaxial bone anchoring device of claim 1, wherein the pressure member has a tapered bottom end configured to engage the inner tapered portion of the insert piece.

9. The polyaxial bone anchoring device of claim 8, wherein an outer surface of the pressure member that extends axially upwards from the tapered bottom end is at least partially cylindrical.

10. A polyaxial bone anchoring device comprising:
    an anchoring element having a shaft for anchoring in a bone and a head;
    a receiving part configured to be pivotably connected to the head, the receiving part having a top end and a bottom end, a longitudinal axis extending through the top end and the bottom end, a channel transverse to the longitudinal axis for receiving a rod, and an accommodation space for accommodating the head;
    an insert piece comprising a seat configured to hold the head in the receiving part; and
    a pressure member positionable at least partially in the accommodation space;
    wherein when the head is held in the seat and the pressure member is held against the head, the head, the insert piece, and the pressure member are insertable together from the bottom end of the receiving part and securable in the receiving part while respective rotational orientations of the head, the insert piece, and the pressure member relative to the longitudinal axis remain constant;
    wherein when the head, the insert piece, and the pressure member are in the receiving part and the head is held in the seat, the anchoring element is configured to be locked at an angle relative to the longitudinal axis of the receiving part when the pressure member directly contacts the head and exerts pressure onto the head.

11. The polyaxial bone anchoring device of claim 10, wherein the head comprises a spherically-shaped outer surface portion, and the seat correspondingly comprises a spherically-shaped inner surface portion.

12. The polyaxial bone anchoring device of claim 10, wherein the insert piece has a spherically-shaped exterior surface portion.

13. The polyaxial bone anchoring device of claim 10, wherein the insert piece is tiltable with respect to the longitudinal axis of the receiving part and with respect to a longitudinal axis of the anchoring element.

14. The polyaxial bone anchoring device of claim 10, wherein the insert piece is configured to be locked at an angle relative to the longitudinal axis of the receiving part when the pressure member exerts pressure on the head.

15. The polyaxial bone anchoring device of claim 10, wherein the head, the insert piece, and the pressure member are insertable together from the bottom end of the receiving part into the receiving part while at least the insert piece is in a tilted configuration relative to the longitudinal axis of the receiving part.

16. A polyaxial bone anchoring device comprising:
   an anchoring element having a shaft for anchoring in a bone and a head;
   a receiving part configured to be pivotably connected to the head, the receiving part having a top end and a bottom end, a longitudinal axis extending through the top end and the bottom end, a channel transverse to the longitudinal axis for receiving a rod, and an accommodation space for accommodating the head;
   an insert piece comprising a seat configured to hold the head in the receiving part; and
   a pressure member positionable at least partially in the accommodation space and comprising a spherically-shaped outer surface portion;
   wherein when the head, the insert piece, and the pressure member are in the receiving part and the head is held in the seat, the insert piece and the pressure member are both tiltable with respect to the longitudinal axis of the receiving part and with respect to a longitudinal axis of the anchoring element, and wherein the anchoring element and the insert piece are configured to be locked at respective angles relative to the longitudinal axis of the receiving part when the pressure member directly contacts the head and exerts pressure onto the head.

17. The polyaxial bone anchoring device of claim 16, wherein the head comprises a spherically-shaped outer surface portion, and the seat correspondingly comprises a spherically-shaped inner surface portion.

18. The polyaxial bone anchoring device of claim 16, wherein the insert piece comprises a spherically-shaped exterior surface portion.

19. The polyaxial bone anchoring device of claim 16, wherein the insert piece and the pressure member are independently tiltable relative to one another.

20. The polyaxial bone anchoring device of claim 16, wherein the pressure member is configured to directly contact the insert piece in the receiving part.

* * * * *

UNITED STATES PATENT AND TRADEMARK OFFICE
CERTIFICATE OF CORRECTION

PATENT NO. : 11,937,852 B2
APPLICATION NO. : 17/404239
DATED : March 26, 2024
INVENTOR(S) : Lutz Biedermann et al.

Page 1 of 1

It is certified that error appears in the above-identified patent and that said Letters Patent is hereby corrected as shown below:

In the Specification

In Column 9, Line 36, delete "6m." and insert -- 6'''. --.

In Column 9, Line 39, delete "6m" and insert -- 6''' --.

In Column 9, Line 52, delete "6m." and insert -- 6'''. --.

In Column 9, Line 55, delete "6m." and insert -- 6'''. --.

In Column 9, Line 59, delete "6m," and insert -- 6''', --.

In Column 10, Line 16, delete "6m." and insert -- 6'''. --.

In Column 10, Line 20, delete "6m" and insert -- 6''' --.

In Column 10, Line 24, delete "6m" and insert -- 6''' --.

In Column 10, Line 39, delete "6''''" and insert -- 6''' --.

In Column 10, Line 44, delete "6m" and insert -- 6''' --.

In Column 10, Line 48, delete "6m" and insert -- 6''' --.

In Column 10, Line 52, delete "6''''" and insert -- 6''' --.

In Column 10, Line 54, delete "6m." and insert -- 6'''. --.

Signed and Sealed this
Second Day of July, 2024

Katherine Kelly Vidal
*Director of the United States Patent and Trademark Office*